(12) United States Patent
Zhong et al.

(10) Patent No.: US 9,568,451 B2
(45) Date of Patent: *Feb. 14, 2017

(54) ENVIRONMENT DETECTING APPARATUS EMPLOYING AN ASYMMETRIC WAVEFORM PULSE GENERATOR

(71) Applicant: University of Electronic Science and Technology of China, Chengdu, Shichuan (CN)

(72) Inventors: Qishui Zhong, Shichuan (CN); Hui Li, Shichuan (CN); dajin Chen, Shichuan (CN); Baihua Li, Guangdong (CN)

(73) Assignee: University of Electronic Science and Technology of China, Chengdu, Sichuan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/932,973

(22) Filed: Nov. 5, 2015

(65) Prior Publication Data

US 2016/0054265 A1   Feb. 25, 2016

Related U.S. Application Data

(63) Continuation of application No. 14/473,793, filed on Aug. 29, 2014, now Pat. No. 9,207,208.

(30) Foreign Application Priority Data

Jun. 17, 2014 (CN) .......................... 2014 1 02701275

(51) Int. Cl.
*H03K 7/08* (2006.01)
*H03K 17/691* (2006.01)
*G01N 27/62* (2006.01)
*H03K 17/10* (2006.01)

(52) U.S. Cl.
CPC .............. *G01N 27/624* (2013.01); *H03K 7/08* (2013.01); *H03K 17/102* (2013.01); *H03K 17/691* (2013.01)

(58) Field of Classification Search
CPC ...... G01N 27/624; H03K 7/08; H03K 17/102; H03K 17/691
See application file for complete search history.

(56) References Cited

U.S. PATENT DOCUMENTS 9,207,208 B2 * 12/2015 Zhong .................. H03K 17/102

* cited by examiner

*Primary Examiner* — Wyatt Stoffa
*Assistant Examiner* — Eliza Osenbaugh-Stewart

(57) ABSTRACT

An environment detecting apparatus employing an asymmetric waveform pulse generator is disclosed. The asymmetric waveform pulse generator comprises a metal oxide semiconductor field effect transistor (MOSFET) bridge circuit that comprises a plurality of MOSFETs for inverting high voltage DC voltage to asymmetric waveform pulses, a pulse-width modulating (PWM) circuit for generating PWM signals, and a plurality of isolation driving circuits corresponding to the plurality of MOSFETs, for controlling switching on/off of the plurality of MOSFETs in the MOSFET bridge circuit based on the PWM signals generated by the PWM circuit. Wherein each of the isolation driving circuits comprises an isolation transformer for isolating the MOSFET bridge circuit from the PWM circuit.

18 Claims, 7 Drawing Sheets

ENVIRONMENT DETECTING APPARATUS EMPLOYING AN ASYMMETRIC WAVEFORM PULSE GENERATOR

CROSS-REFERENCE TO RELATED APPLICATIONS

This application is a continuation of U.S. patent application Ser. No. 14/473,793, filed Aug. 29, 2014, now U.S. Pat. No. 9,207,208, which is incorporated herein by reference in its entirety.

TECHNICAL FIELD

The present invention is related to environment detecting apparatuses, and more particularly to an asymmetric waveform pulse generator of an environment detecting apparatus.

BACKGROUND

With the development of human society, people have stronger and stronger expectation on living quality especially on environmental quality, which leads to a new research field for real time monitoring surrounding environment. Currently-used environment detecting apparatus have the shortcomings such as high cost, huge space occupation, low detecting efficiency, and so on, and could not meet people's daily use requirements. In comparison, ion detectors based on high-field asymmetric waveform ion mobility spectrometry (FAIMS) technology are become more and more popular in environmental detection, in that the ion detectors have the advantages of high sensitivity, fast detecting speed, wide detecting product ranges, small space occupation and low cost. Generally, the ion detectors are widely used in environmental monitoring, public security management, and so on.

FAIMS technology is formed based on Mason and McDaniel's experimental discovery result that ion mobility K is related to strength of electric field enforced thereon. Under a lower electric field strength, for example the strength of the lower electric field is lower than 11000V/cm, the ion mobility K is not influenced by the lower electric field strength. However, when under a higher electric field, for example the strength of the higher electric field is higher than 11000 V/cm, the ion mobility K would change in accordance with the higher electric field strength in a nonlinear manner. Under a higher electric field, a relationship between the ion mobility K and the electric field strength E can be expressed as:

$$K=K_0*[1+\alpha_1(E/N)^2+\alpha_2(E/N)^4+L] \quad (1)$$

Where, $K_0$ is a mobility of ion in the lower electronic field, $\alpha$ is ion mobility coefficient, E is the electric field strength, and N is gas density. Here if:

$$\alpha(E)=[\alpha_1(E/N)^2+\alpha_2(E/N)^4+L] \quad (2)$$

The formula (1) could be simplified as:

$$K=K_0*[1+\alpha(E)] \quad (3)$$

According to formula (3), the ion mobility K is specific for each particular kind of ion, which makes, those ions having same or similar mobility in lower electric field strength could be isolated under higher electric field strength.

In practice, when loading an impulsive voltage with high frequency and asymmetric waveform on a pair of electrode panels that are placed face to face and subsequently form a narrow space, the narrow space would thus become an electric field. When air flow carrying ions flows through the narrow space in a first direction, the ions would vibrate along a second direction of the electric field. Under a composed speed of speeds in the first direction and the second direction, the ions with different mobility would be isolated from each other. The composed speed has an X-component in a direction along the narrow space and a Y-component in a direction vertical to the direction along the narrow space. Meanwhile, if another suitable direct current (DC) voltage is loaded on the pair of electrode panels, an electric field generated by the suitable direct current would act in an opposite direction to that of the Y-component on the ions and subsequently the Y-component speed of some particular ions would be set off. Consequently, the particular ions only has the X-component speed, which would lead the particular ions move along the narrow space and eventually pass through the narrow space. At the same time, ions other than the particular ions would move to the electric panel under the combined effect of their X-component and Y-component speed. In this way, the particular ions would be checked out.

In said ion detecting process, a generator to generate the voltage with asymmetric waveform meeting requirements of the FAIMS is very important, in that the waveform would directly influenced the performance of the FAIMS ion detector.

BRIEF DESCRIPTION OF THE DRAWINGS

The details as well as other features and advantages of this invention are set forth in the remainder of the specification and are shown in the accompanying drawings.

DETAILED DESCRIPTION OF THE EMBODIMENTS

In the following description, for purposes of explanation and not limitation, specific details are set forth such as particular architectures, interfaces, techniques, etc. in order to provide a thorough understanding of the present invention. However, it will be apparent to those skilled in the art that the present invention may be practiced in other embodiments that depart from these specific details. In other instances, detailed descriptions of well-known devices, circuits, and methods are omitted so as not to obscure the description of the present invention with unnecessary detail.

Figure 1:
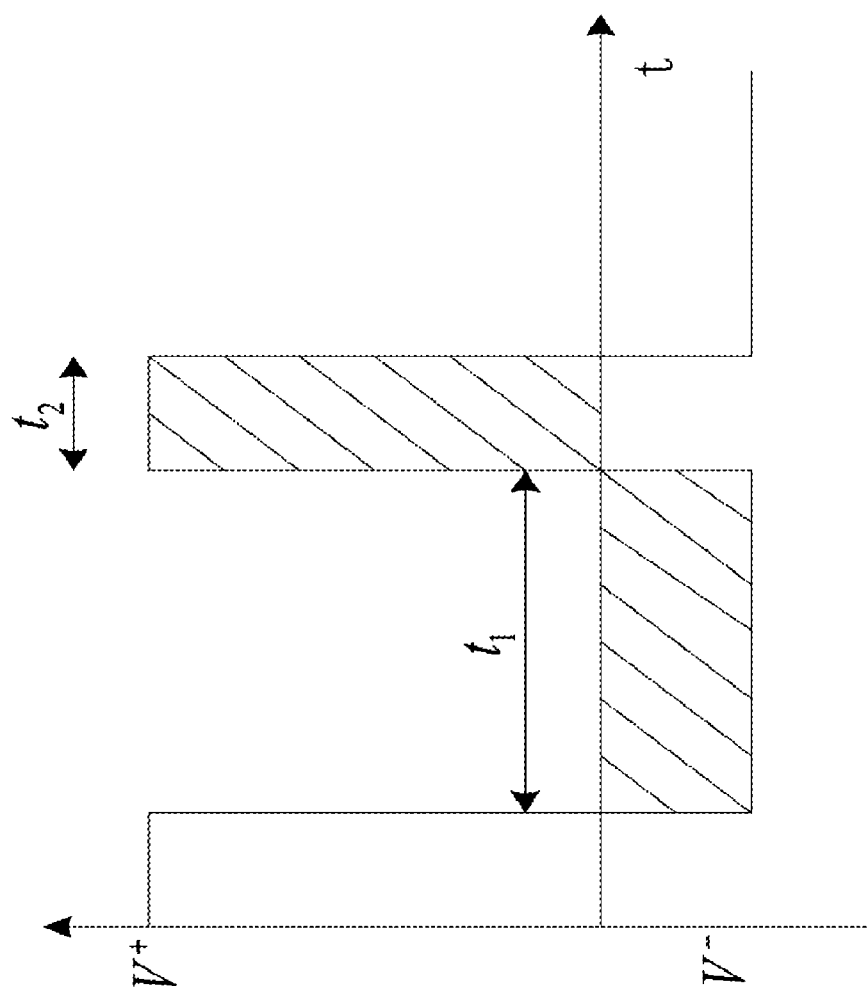
FIG. 1 is an ideal asymmetric waveform required by a high-field asymmetric waveform ion mobility spectrometry (FAIMS) system.

In the exemplary embodiment of the present invention, in a high-field asymmetric waveform ion mobility spectrometry (FAIMS) ion detector, a generator for generating high frequency and high voltage asymmetric waveform pulse is relatively important. An ideal asymmetric waveform is shown as FIG. 1, where the shadow areas on two sides of the X-axle are equal, that is:

$$V^+ \times t_2 = V^- \times t_1$$

In order to generate said ideal waveform, in a preferred embodiment of the present invention, the high voltage high frequency asymmetric waveform pulse generator 200 comprises a MOSFET half-bridge circuit 203 for inverting high voltage direct current input into high voltage pulse.

Figure 2:
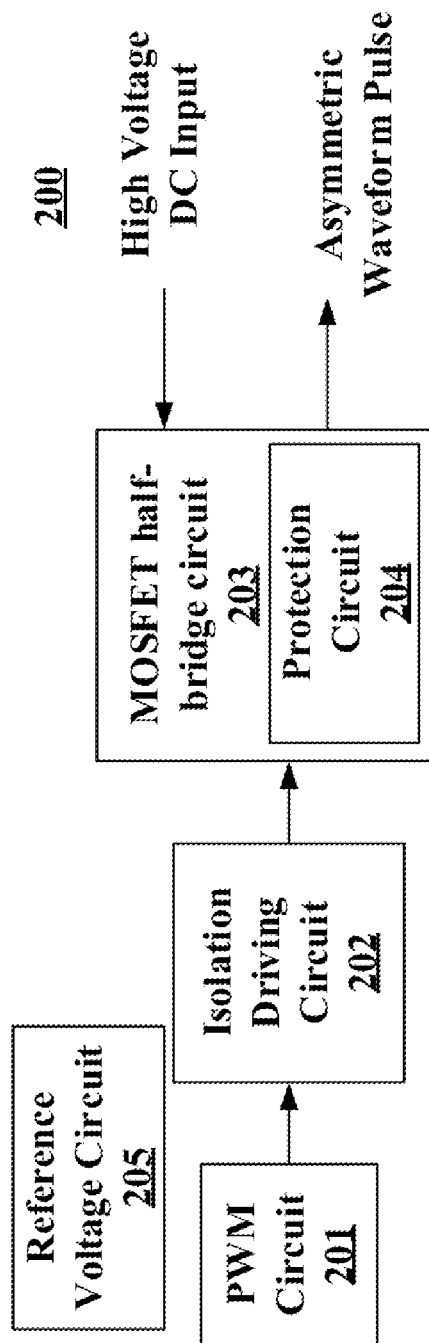
FIG. 2 is a schematic diagram of a high frequency high voltage asymmetric waveform pulse generator according to a preferred embodiment.

As shown in FIG. 2, the high frequency high voltage asymmetric waveform pulse generator 200 according to the preferred embodiment of the present invention comprises a PWM (Pulse Width Modulation) circuit 201, an isolation driving circuit 202, a MOSFET half-bridge circuit 203, a protection circuit 204 and a reference voltage circuit 205. The PWM circuit 201 is used for providing negative and positive PWM signals with adjustable duty cycle, frequency and dead time. The isolation driving circuit 202 is used for controlling the MOSFETs in the MOSFET half-bridge circuit 203 respectively on or off according to the positive and negative PWM signals output from the PWM circuit 201. The MOSFET half-bridge circuit 203 is used for inverting high voltage direct current input, such as 2 kV direct current, and outputting high voltage pulse, for example, in the form of square wave. The protection circuit 204 is used for protecting the MOSFETs in the MOSFET half-bridge circuit 203 either in static state or in dynamic state from being burnt by over-voltage or over-current.

The reference voltage circuit 205 provides various reference voltages for modules or chips in above-mentioned circuits. In a preferred embodiment of the present invention, the various reference voltages comprise 5V and 12V. For ensuring the isolation driving circuit 202 to efficiently drive the MOSFETs in the MOSFET half-bridge circuit 203, in a preferred embodiment of the present invention, the reference voltage circuit 205 comprises linear transforming chips LT1084-12 and LT1084-5 provided by Linear Technology, to transforming main alternating voltage 220V to direct current voltages, such as 12V and 5V accompanying with suitably designed transforms and rectifier bridges.

Figure 3:
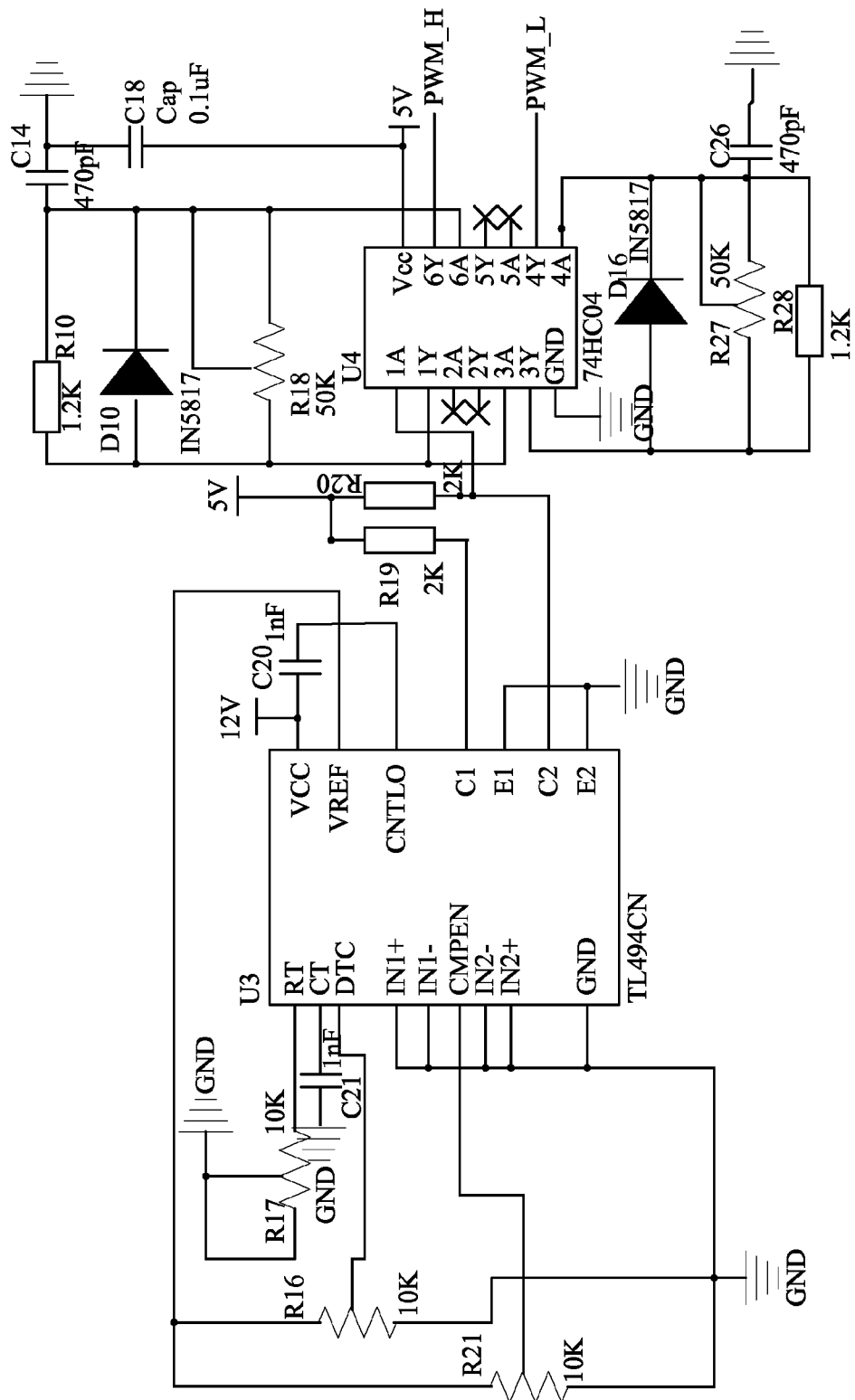
FIG. 3 is a detailed circuit of a PWM circuit in accordance with an exemplary disclosure of the present invention.

FIG. 3 shows the PWM circuit 201 in a preferred embodiment of the present invention. In the preferred embodiment of the present invention, the PWM circuit 201 comprises a TL494CN chip produced by Texas Instruments company for generating pulse width modulation (PWM) signals, a NOT-gate circuit 74HC04 for reversing and reshaping the PWM signals generated by the TL494CN chip, and a dead zone generation circuit for generating positive and negative PWM signals to control the half bridge circuit 203.

As shown in FIG. 3, the TL494CN chip is driven by 12V direct current voltage, and decoupled by a ceramic capacitor C20. A RC oscillator circuit composed of an adjustable resistor R17 and a capacitor C21 respectively connected to a RT pin and a CT pin of the TL494CN chip controls the frequency of the PWM signals, by changing resistance of the adjustable resistor R17, the frequency of the generated PWM signals could be adjusted correspondingly. In the embodiment, an adjustable resistor R16 is connected between a reference voltage and a duty cycle (DTC) pin of the TL494CN chip, by changing the resistance of the adjustable resistor R16 could change the duty cycle of the generated PWM signals. In a preferred embodiment of the present invention, because the PWM signals generated by the TL494CN chip are single-channel signals, for simultaneously controlling the upper and the lower arms of the MOSFET half-bridge circuit 203, the generated signal-channel PWM signals are transmitted to a NOT-gate circuit, such as the 74HC04 type chip in FIG. 3, to generate two-channel PWM signals. In the preferred embodiment of the present invention, the NOT-gate circuit, i.e., the 74HC04 type chip comprises six NOT-gates.

Firstly, the single-channel PWM signals are input to a first NOT-gate by way of the pin 1A of the NOT-gate circuit, wherein the output of the first NOT-gate is negative to the input thereof. That means the output PWM signals by the first NOT-gate are negative to the single-channel PWM signals. In this embodiment, the PWM signals output by the first NOT-gate from the pin 1Y is divided into two parts, one part enters into a sixth NOT-gate by way of a first dead circuit, and the other part is transmitted into a third NOT-gate and eventually input to a fourth NOT-gate by way of a second dead circuit. After the processing procedure, the polarity of the PWM signal PWM_H output from a pin 6Y of the sixth NOT-gate is same to that of the single-channel PWM signals, and the polarity of the PWM signal PWM_L output from a pin 4Y of the fourth NOT-gate is negative to that of the single-channel PWM signals. In this way, two-channel PWM signals with negative polarity are generated.

In a preferred embodiment of the present invention, the first dead circuit comprises a resistor R10, a diode D10 and an adjustable resistor R18 which are connected in parallel and between the pins 1A and 6A of the NOT-gate circuit, the second dead circuit comprises a resistor R28, a diode D16 and an adjustable resistor R27 which are connected in parallel and between the pins 3Y and 4A of the NOT-gate circuit. Changing the resistance of the adjustable resistor R18 or R27 respectively in the first and the second dead circuits could change the dead time of the first and second dead circuits respectively, so as to avoid simultaneously switching on/off the upper or lower arms of the half-bridge circuit 203, and subsequently avoid conducting the high voltage direct current to the ground, thus improve the reliability of the high frequency high voltage asymmetric waveform pulse generator 200 of the present invention.

In the high frequency high voltage asymmetric waveform pulse generator 200 according to one preferred embodiment of the present invention, the power of the PWM signals PWM_H and PWM_L are relatively low as not to drive the MOSFETs in the MOSFET half-bridge circuit 203, so that the power of the PWM signals PWM_H and PWM_L should be amplified to be able to switch on/off the MOSFETs in the MOSFET half-bridge circuit 203. When peak voltage of the MOSFET half-bridge circuit 203 is up to 2 kV, and/or the frequency thereof is up to 200 kHz, those low voltage circuits, such as the PWM circuit 201, would be seriously disturbed even destroyed by the peak voltage originating from the MOSFET half-bridge circuit 203. For this reason, in the exemplary asymmetric waveform pulse generator 200 according to one of the present invention, the isolation driving circuit 202 is employed to eliminate the disturb of the peak voltage to the low voltage circuits, such as the PWM circuit 201, consequently improve the quality of the PWM signals generated by the PWM circuit 201.

Figure 5:
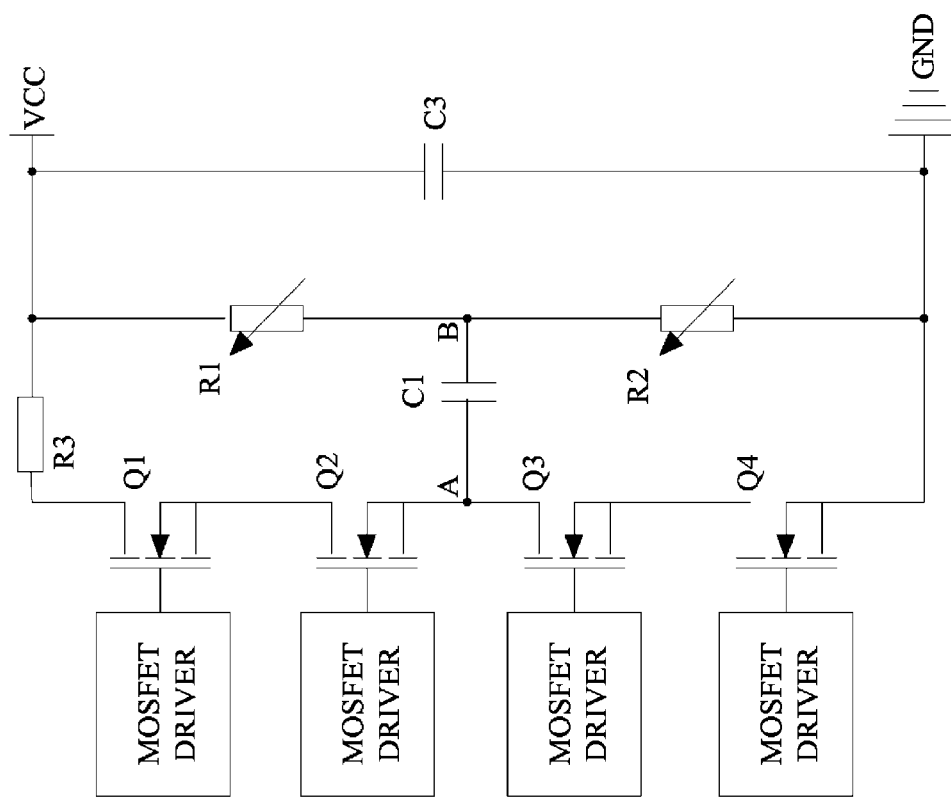
FIG. 5 is a detailed circuit of a MOSFET half-bridge circuit in accordance with an exemplary disclosure of the present invention.

Because the PWM signals to drive each MOSFET in the half-bridge circuit 203 should be isolated, as well as the upper and lower arms of the MOSFET half-bridge circuit 203 in a preferred embodiment of the present invention are structured with two MOSFETs connected in series, in this embodiment, total four channels of PWM signals isolated from each other are needed, as shown in FIG. 5. The isolation driving circuit 202 according the preferred embodiment of the present invention has the advantages of simple structure and high isolation, in that each MOSFET has an independent isolation driving circuit.

In a preferred embodiment of the present invention, the isolation driving circuit 202 of each MOSFET in the MOSFET half-bridge circuit 203 are same structured, for simplicity of description, the isolation driving circuit 202 of the MOSFET Q1 would be detailed described in the following specification. Isolation driving circuits 202 of the other MOSFET Q2, Q3 and Q4 are same to that of the MOSFET Q1, and would not be described in detail.

In the preferred embodiment, the isolation driving circuit 202 of the MOSFET Q1 comprises the IXDD409 type driver produced by IXYS company, the peak current of the IXDD409 type driver is up to 9 A, which can greatly fasten the speed of the MOSFET Q1 being switch on so as to lower loss of the MOSFET Q1. The IXDD409 type driver is powered by 12V direct current voltage, and decoupled by the capacitor C1. For ensuring providing enough driving current to drive the MOSFET Q1 switch on, in a preferred embodiment of the present invention, a capacitor C5 is employed as power storage of the IXDD409 type driver. An EN pin of the IXDD409 type driver is the enable end and is connected to high level signal, an IN pin receives input PWM signals, two OUT pins output driving signals, voltage difference of positive and negative amplitude of which could be up to 12V. In a preferred embodiment of the present invention, a gate-break-over voltage of the employed IXYS 3N120 type MOSFET Q1 is 3.5V, the 12V driving signals could ensure switching on of the MOSFET Q1. The driving signals output by the IXDD409 type driver pass through the capacitor C2 and the isolation transformer T1 so as to be isolated from the high voltage circuit, wherein a ratio of the isolation transformer T1 is 1:1, detailed parameters of the isolation transformer T1 is shown in Sheet 1.

connected in series face to face so as to secure the driving signals transmitted to the gates of the MOSFETs not beyond specified voltage amplitude, to protect the MOSFETs from being destroyed.

FIG. 5 shows the MOSFET half-bridge circuit 203 in accordance with a preferred embodiment of the present invention. Under the effect of asymmetric high field, two panels of an FAIMS ion detector (not shown) according to the preferred embodiment of the present invention can be regarded as an equivalent capacitor, such as the capacitor C1 illustrated in FIG. 5. The connection points VCC and GND are respectively connected to the positive and negative of the high voltage direct current input, the capacitor C3 connected between the points VCC and GND is a high voltage storage capacitor, the resistor R3 connected between the point VCC and the drain of the MOSFET Q1 is a non-inductance resistor to limit the current. Gates of the MOSFET Q1, Q2, Q3 and Q4 are respectively connected to the isolation driving circuit 202 to receive the driving signals. The drain of the MOSFET Q1 receives the high voltage direct current from the connection point VCC by way of the resistor R3, a source of the MOSFET Q1 is connected to a drain of the MOSFET Q2, thus the MOSFET Q1 and the MOSFET Q2 are connected in series and collectively form the upper arm of the half-bridge circuit 203. The source of the MOSFET Q2 is connected to the drain of the MOSFET Q3, and the source of the MOSFET Q3 is connected to the drain of the MOSFET Q4, thus the MOSFET Q3 and the MOSFET Q4 are connected in series and collectively form the lower arms of the half-bridge circuit 203. A source of the MOSFET Q4 is connected to the connection point GND.

The source of the MOSFET Q2 and the drain of the MOSFET Q3 is connected at connection point A, that is, the connection pint A of the upper and lower arms of the half-bridge circuit 203 is one output of the asymmetric waveform pulse generator 200 of the present invention, and is connected to one of the two panels of the ion detector, so

| | | | Sheet 1 Spce of isolation transformet | | | |
|---|---|---|---|---|---|---|
| Ratio | Dielectric Strength $V_p$(kV) | Trigger Manner | Frequency Fp (Hz) | Specified ∫udt (μVS) | Input Voltage Amplitude V1 (V) | Pulse Width $t_n$ (μS) | Output Voltage Amplitude V2 (V) |
| 1:1 | 3.1 | pulse | 250k | 200 | 15 | 5 | 15 |

Figure 4:
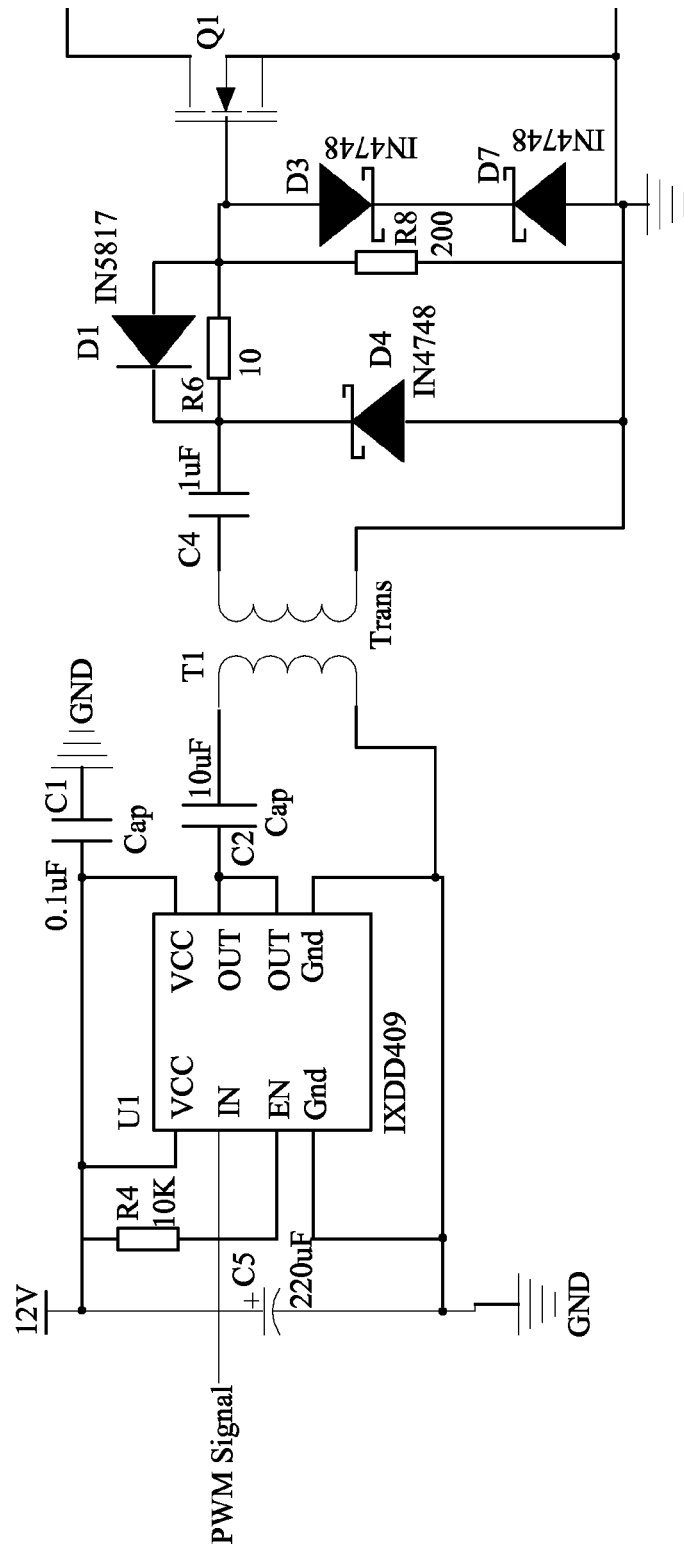
FIG. 4 is a detailed circuit of an isolation driving circuit in accordance with an exemplary disclosure of the present invention.

In a preferred embodiment of the present invention, the capacitors C2 and C4 is employed to block direct current signals, a Zener diode D4 coupled o the isolation transformer T1 is used to prevent the isolation transformer T1 from outputting over-lower voltage. The gate of the MOSFET Q1 is connected to a resistor R6, for reducing ring phenomenon and EMI. In a preferred embodiment of the present invention, the MOSFET Q1 is an N-type transistor. In a switching-on procedure, driving signals are transmitted from the isolation transformer T1, through a resistor R6, and eventually to the gate of the MOSFET Q1, in a switching-off procedure, the driving signals are transmitted from the gate of the MOSFET Q1, through the diode D1, and eventually to the isolation transformer T1. The diode D1, with an anode connected to a gate of the MOSFET Q1 and a cathode connected to the isolation transformer T1, is used for accelerating switching off of the MOSFET Q1, to ensure smooth switching between on and off of the MOSFET Q1, Q2, Q3 and Q4. In FIGS. 4, D3 and D7 are Zener diodes, which are that the connection point A could be regarded as connected to one end of the equivalent capacitor C1. When the MOSFETs Q1 and Q2 in the upper arm are simultaneously switched on, electric potential of the point A is same to that of the connection point VCC, and when the MOSFETs Q3 and Q4 in the lower arm are simultaneously switched on, the electric potential of the point A is same to that of the connection point GND. In the preferred embodiment, the electric potential of the connection point GND is 0V. The adjustable resistor R1 and R2 are connected in series between the drain of the MOSFET Q1 and the source of the MOSFET Q4. In other words, the resistor R1 and R2 are connected in series between positive and negative of the high voltage direct current input. A connection point B structured between the resistors R1 and R2 is another output of the asymmetric waveform pulse generator 200 of the present invention, and is connected to another one of the two panels of the ion detector, so that the connection point B could be regarded as connected to another end of the equivalent capacitor C1. By altering resistance of the resistors R1 and R2, the electric potential of the connection point B could be changed between 0V and VCC continuously, accompanying with adjusting the frequency and duty ratio of the PWM signals that drives the MOSFETs, asymmetric waveform needed by the FAIMS would be generated between the equivalent capacitor C1, i.e., between the connection points A and B. In a preferred embodiment of the present invention, the N-type MOSFETs Q1, Q2, Q3 and Q4 are 3N120-type MOSFETs produced by IXYS company.

In general, when a pulse circuit works with high frequency, voltage and current loaded upon MOSFETs in the pulse circuit change very fast, which are prone to making the MOSFETs destroyed. Therefore, in a preferred embodiment of the present invention, a protection circuit is connected in parallel between the source and drain of each of the MOSFETs Q1, Q2, Q3 and Q4, for absorbing overshoot voltage to prevent the MOSFETs Q1, Q2, Q3 and Q4 from being broken down due to over voltage, as well as reducing overshoot of rising edge of the output pulse by the asymmetric waveform pulse generator 200, so as to output high quality asymmetric waveform.

Figure 6:
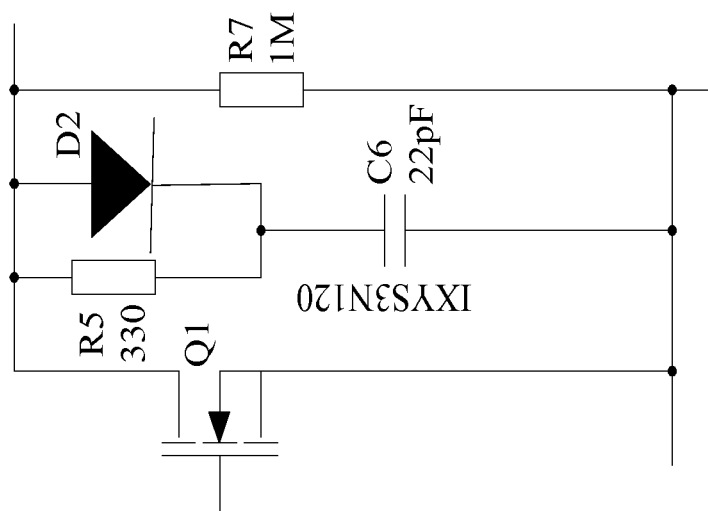
FIG. 6 is a detailed circuit of a protection circuit in accordance with an exemplary disclosure of the present invention.

FIG. 6 shows a protection circuit of the MOSFET Q1, other MOSFETs Q2, Q3 and Q4 have same structure of protection circuits to that of the MOSFET Q1, for the simplicity of description, the specification would only describe the structure of the protection circuit 204 of the MOSFET Q1.

When the MOSFET Q1 is switched off, the high voltage direct current input loaded upon the drain of the MOSFET Q1 charges the capacitor C6 by way of the diode D2. When the MOSFET Q1 is switch on, the power stored in the capacitor C6 is discharged by way of the resistor R5. The diode D2 is used to restrain peak voltage oscillation upon the drain of the MOSFET Q1, the diode D2 is used to prevent the capacitor C6 from discharging when the MOSFET Q1 is switched on, so as to reduce the load of the MOSFET Q1 when switched on. In a preferred embodiment of the present invention, power are transferred from the MOSFET Q1 to the capacitor C6, and eventually depleted by the resistor R5, so as to protect the MOSFET Q1. In a preferred embodiment of the present invention, switch-on time of the MOSFET Q1 is bigger than the discharging time of the capacitor C6, that is:

$$\tau_{RC} < t_{on} \quad (5)$$

Here, $\tau_{RC}$ is a time constant of the RC circuit composed of the resistor R5 and the capacitor C6, $t_{on}$ is the switch-on time of the MOSFET Q1.

Because electronic features of the MOSFETs Q1, Q2, Q3 and Q4 are different from each other, divided voltages upon the MOSFETs Q1, Q2, Q3 and Q4 would be different from each other, the worst situation is the divided voltage upon one of the MOSFET Q1, Q2, Q3 and Q4 exceeds the value of permissible voltage of the corresponding MOSFET and destroys it. For this reason, in a preferred embodiment of the present invention, four equate resistors with same resistance are connected respectively in parallel to the sources and drains of the MOSFETs Q1, Q2, Q3 and Q4 in the upper and lower arms, such as the resistor R7 electronically connected in parallel to the source and drain of the MOSFET Q1. In this way, the voltages loaded upon the MOSFETs Q1, Q2, Q3 and Q4 could reach to be same, so as to achieve protection to the MOSFETs Q1, Q2, Q3 and Q4.

In a preferred embodiment of the present invention, the work voltages of the above-mentioned chips comprise 5V and 12V direct current (DC) voltages. For ensuring the isolation driving circuit 202 having enough power to fast drive the MOSFETs to switch on or off, linear transformer chips LT1084-12 and LT1084-5 produced by Linear Technology, a transformer T and a rectification bridge collectively form the reference voltage circuit 205, to transform utility voltage, such as alternating current (AC) voltage 220V, to DC voltages, such as 12V and 5V. Detailed diagram of the reference voltage circuit 205 is shown in FIG. 7.

Figure 7:
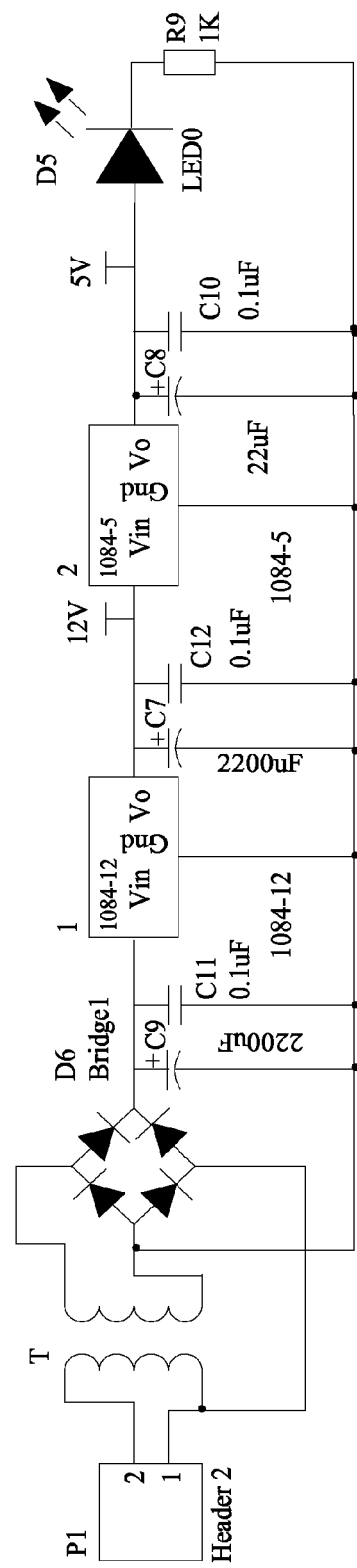
FIG. 7 is a detailed diagram of a reference voltage circuit according to a preferred embodiment of the present disclosure.

The interface P1 in FIG. 7 receives utility voltage, such as AC 220V. The utility voltage is then transformed by the transformer T to AC voltage 18V. The AC voltage 18V is subsequently rectified by the rectification bridge to DC voltage. Finally, the chips LT1084-12 and LT1084-5 respectively transform the rectified DC voltage as 12V and 5V DC voltages, which provide power to various chips in the asymmetric waveform pulse generator 200. The most output current of the LT1084 series is up to 5 A, which could meet the requirements of the asymmetric waveform pulse generator 200 of the present invention.

In the preferred embodiment of the present invention, a peak voltage of the high frequency high voltage asymmetric waveform pulse generator 200 can reach to 2 kV, the frequency thereof is 200 kHz, and rising edge and falling edge of the asymmetric waveform pulse output by the pulse generator 200 are both within 10 ns, which means the quality of the asymmetric waveform is good. In addition, the structure of the pulse generator 200 is simple, wherein the frequency, duty cycle and dead time of the PWM circuit 201 are adjustable, and the power consumption is low, which collectively makes the asymmetric waveform pulse generator 200 meet the requirements of the FAIMS system.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. An environment detecting apparatus comprising an asymmetric waveform pulse generator for transforming high voltage direct current (DC) voltage to asymmetric waveform pulse to detect and isolate various ions existed in a particular environment, the asymmetric waveform pulse generator comprising:
   a metal oxide semiconductor field effect transistor (MOSFET) bridge circuit comprising a plurality of MOSFETs for inverting the high voltage DC voltage to the asymmetric waveform pulse;
   a pulse-width modulating (PWM) circuit for generating PWM signals;
   a plurality of isolation driving circuits corresponding to the plurality of MOSFETs, for controlling switching on/off of the plurality of MOSFETs in the MOSFET bridge circuit based on the PWM signals generated by the PWM circuit;
   wherein each of the isolation driving circuits comprises an isolation transformer for isolating the MOSFET bridge circuit from the PWM circuit.

2. The environment detecting apparatus of claim 1, further comprises a plurality of protection circuits each connecting to a drain of corresponding one of the MOSFETs for absorbing overshoot voltages.

3. The environment detecting apparatus of claim 1, further comprises a plurality of resistors each connecting in parallel to a source and a drain of corresponding one of the MOSFETs, wherein the resistors have same resistance.

4. The environment detecting apparatus of claim 1, wherein the PWM signals comprise two channel signals respective in positive and in negative.

5. The environment detecting apparatus of claim 4, wherein the MOSFETs are four, two of which collectively forming an upper arm of the MOSFET bridge circuit, and remaining two collectively forming a lower arm.

6. The environment detecting apparatus of claim 5, further comprising two adjustable resistors connected in series between positive and negative poles of the high voltage DC voltage.

7. The environment detecting apparatus of claim 6, wherein a connection point of the upper and lower arms is connected to one of the two panels of the FAIMS ion detector, and a connection point of the two adjustable resistors is connected to another one of the two panels of the ion detector.

8. The environment detecting apparatus of claim 1, wherein the PWM circuit comprises a TL494CN chip for generating PWM signals, a NOT-gate circuit for reversing and reshaping the PWM signals generated by the TL494CN chip, and a dead zone generation circuit for generating positive and negative PWM signals to control the half bridge circuit.

9. The environment detecting apparatus of claim 8, wherein the PWM circuit comprises a RC oscillator circuit composed of an adjustable resistor (R17) and a capacitor (C21) to control the frequency of the PWM signals.

10. The environment detecting apparatus of claim 8, wherein the first dead circuit comprises a resistor (R10), a diode (D10) and an adjustable resistor (R18) which are connected in parallel, and the second dead circuit comprises a resistor (R28), a diode (D16) and an adjustable resistor (R27) which are connected in parallel.

11. The environment detecting apparatus of claim 10, wherein the dead time of the first and second dead circuits are adjustable by changing the resistance of the adjustable resistors (R18) and (R27) respectively, so as to avoid simultaneously switching on/off the arms of the half-bridge circuit.

12. The environment detecting apparatus of claim 1, wherein each of the isolation driving circuits comprises a Zener diode coupled to the isolation transformer to prevent the isolation transformer from outputting over-lower voltage.

13. The environment detecting apparatus of claim 12, wherein each of the isolation driving circuits comprises a diode, with an anode connected to a gate of a corresponding MOSFET and a cathode connected to the isolation transformer.

14. A method of detecting and isolating various ions in a particular environment, comprising:
generating an asymmetric waveform pulse by inverting a high voltage direct current (DC) voltage using a metal oxide semiconductor field effect transistor (MOSFET) bridge circuit having a plurality of MOSFETs;
generating PWM signals using a pulse-width modulating (PWM) circuit;
controlling switching on/off of a plurality of MOSFETs in the MOSFET bridge circuit based on the PWM signals generated by the PWM circuit; and
isolating the MOSFET bridge circuit from the PWM circuit.

15. The method of claim 14, further comprising absorbing overshoot voltage by connecting each of a plurality of protection circuits to a drain of a corresponding one of the MOSFETs.

16. The method of claim 14, wherein the PWM signals comprise two channel signals in positive and in negative, respectively.

17. The method of claim 14, wherein the plurality of MOSFETs include two MOSFETs collectively forming an upper arm of the MOSFET bridge circuit, and two other MOSFETs collectively forming a lower arm of the MOSFET bridge circuit.

18. The method of claim 17, further comprising adjusting resistors connected in series between positive and negative poles of the high voltage DC voltage.

* * * * *